(12) United States Patent
Okuyama

(10) Patent No.: US 7,404,326 B2
(45) Date of Patent: Jul. 29, 2008

(54) ULTRASONIC PROBE AND ULTRASONIC DIAGNOSTIC SYSTEM

(75) Inventor: Eitaro Okuyama, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 359 days.

(21) Appl. No.: 11/402,565

(22) Filed: Apr. 12, 2006

(65) Prior Publication Data
US 2006/0232285 A1 Oct. 19, 2006

(30) Foreign Application Priority Data
Apr. 13, 2005 (JP) ............... 2005-115624

(51) Int. Cl.
G01N 29/26 (2006.01)
A61B 8/00 (2006.01)

(52) U.S. Cl. ............... 73/633; 73/620; 73/622; 600/437; 600/447

(58) Field of Classification Search ............ 73/633, 73/620, 621, 622, 623; 600/437, 444–447
See application file for complete search history.

(56) References Cited

U.S. PATENT DOCUMENTS

| | | | |
|---|---|---|---|
| 5,351,692 A | 10/1994 | Dow et al. | |
| 5,450,851 A * | 9/1995 | Hancock | 600/462 |
| 5,721,463 A | 2/1998 | Snyder | |
| 6,102,863 A | 8/2000 | Pflugrath et al. | |
| 6,471,654 B2 | 10/2002 | Ohara et al. | |
| 6,551,245 B1 * | 4/2003 | Irioka et al. | 600/444 |
| 6,645,151 B2 * | 11/2003 | Irioka et al. | 600/459 |
| 6,709,398 B2 | 3/2004 | Umeda et al. | |
| 6,890,301 B2 * | 5/2005 | Jago et al. | 600/437 |
| 2005/0215905 A1 | 9/2005 | Hasegawa et al. | |
| 2006/0173330 A1 * | 8/2006 | Kim | 600/445 |

* cited by examiner

Primary Examiner—Hezron E. Williams
Assistant Examiner—Jacques M. Saint-Surin
(74) Attorney, Agent, or Firm—Armstrong Teasdale LLP (57) ABSTRACT

With a view to provide a probe able to suppress bending of a cable with a mechanical scan, the probe comprises a transducer for interconversion between an ultrasonic wave and an electrical signal, a shell for holding the transducer, a case for accommodating the shell, a motor for moving the shell pivotally about a pivot shaft with respect to the case, a guide bar provided in the shell so as to extend in parallel with the pivot shaft, and coaxial cables extending from the transducer to the guide bar, wound round the guide bar and then extending out form the shell.

8 Claims, 6 Drawing Sheets

ULTRASONIC PROBE AND ULTRASONIC DIAGNOSTIC SYSTEM

CROSS REFERENCE TO RELATED APPLICATIONS

This application claims the benefit of Japanese Application No. 2005-115624 filed Apr. 13, 2005.

BACKGROUND OF THE INVENTION

The present invention relates to an ultrasonic probe and an ultrasonic diagnostic system.

As an ultrasonic scan method using an ultrasonic probe there is known a mechanical scan method wherein a transducer is driven mechanically to effect scan. The ultrasonic probe used in the scan method is for example provided with a drive unit which not only holds the transducer but also moves the transducer pivotally in a scan direction. A cable extending from the transducer is once clipped by a clip portion provided in the drive unit and then extends to a body side of an ultrasonic diagnostic system. Since the cable is clipped by the clip portion of the drive unit, the distance between the transducer and the cable is kept almost constant also during scan, whereby the load imposed on the connection between the transducer and the cable is diminished.

However, since the cable is fixed to the probe at any position extending to the system body side from the clipped position, the cable is bent at the clipped position as the scanning operation proceeds. The bending of the cable causes various inconveniences. For example, since stress concentration occurs in the cable due to the bending, the service life of the cable becomes shorter. Particularly, in the case of the cable used in the aforesaid mechanical scan type probe, bending and stretching are repeated as the scanning operation proceeds and therefore it is important to suppress bending of the cable. Further, when the shape of the clip portion is to be designed so as to suppress the stress concentration or the like, it is required for the design to be a precise design. Especially, in the case of a small-sized probe to be inserted into the body cavity, a high accuracy is required.

SUMMARY OF THE INVENTION

It is an object of the present invention to provide an ultrasonic probe which permits suppression of a cable bending caused by a mechanical scan, as well as an ultrasonic diagnostic system using such an ultrasonic probe.

An ultrasonic probe according to the present invention comprises a transducer for interconversion between an ultrasonic wave and an electric signal, a holding member for holding the transducer, a case member for accommodating the holding member, a driving unit for moving the holding member pivotally about a predetermined pivot shaft with respect to the case member, a guide bar provided in the holding member so as to extend substantially in parallel with the pivot shaft, and a cable extending from the transducer to the guide bar, wound round the guide bar and then extending out from the holding member.

Preferably, the case member has a cable fixing portion for fixing the cable extending out from the holding member, and the length of the cable from the transducer to the cable fixing portion is set so that the cable is wound with a margin round the guide bar.

Preferably, the holding member is formed in the shape of a cylinder around the pivot shaft, the transducer is provided in a side face of the cylinder, a slot is formed in the side face of the cylinder at a position opposite to the transducer, the guide bar is provided in the slot at a position where it is exposed from the slot, and the cable passes through the inside of the cylinder from the transducer, extends to the guide bar and is wound round the guide bar, then extends to the outside of the cylinder from the slot.

Preferably, a sectional shape of the guide bar is a circular shape having a diameter larger than the thickness of the side face of the cylinder in the slot.

Preferably, the plurality of transducer are provided in the axial direction of the pivot shaft, the plurality of cables are provided corresponding respectively to the plural transducers, and the guide bar has such a length as covers the plural transducers in the axial direction of the pivot shaft.

Preferably, adjacent ones of the plural cables are wound in mutually opposite directions round the guide bar.

Preferably, the case member has an inserting portion capable of being inserted into the body cavity of a subject, and the holding member is accommodated in a tip of the inserting portion.

An ultrasonic diagnostic system according to the present invention comprises a probe for radiating an ultrasonic wave to a subject and receiving the ultrasonic wave reflected from the subject, and a system body for generating an image of the subject on the basis of a signal provided from the probe, the probe comprising: a transducer for interconversion between an ultrasonic wave and an electric signal; a holding member for holding the transducer; a case member for accommodating the holding member; a driving unit for moving the holding member pivotally about a predetermined pivot shaft with respect to the case member; a guide bar provided in the holding member so as to extend substantially in parallel with the pivot shaft; and a cable extending from the transducer to the guide bar, wound round the guide bar and then extending out from the holding member.

According to the ultrasonic probe of the present invention it is possible to suppress bending of the cable caused by a mechanical scan.

DETAILED DESCRIPTION OF THE INVENTION

Figure 1:
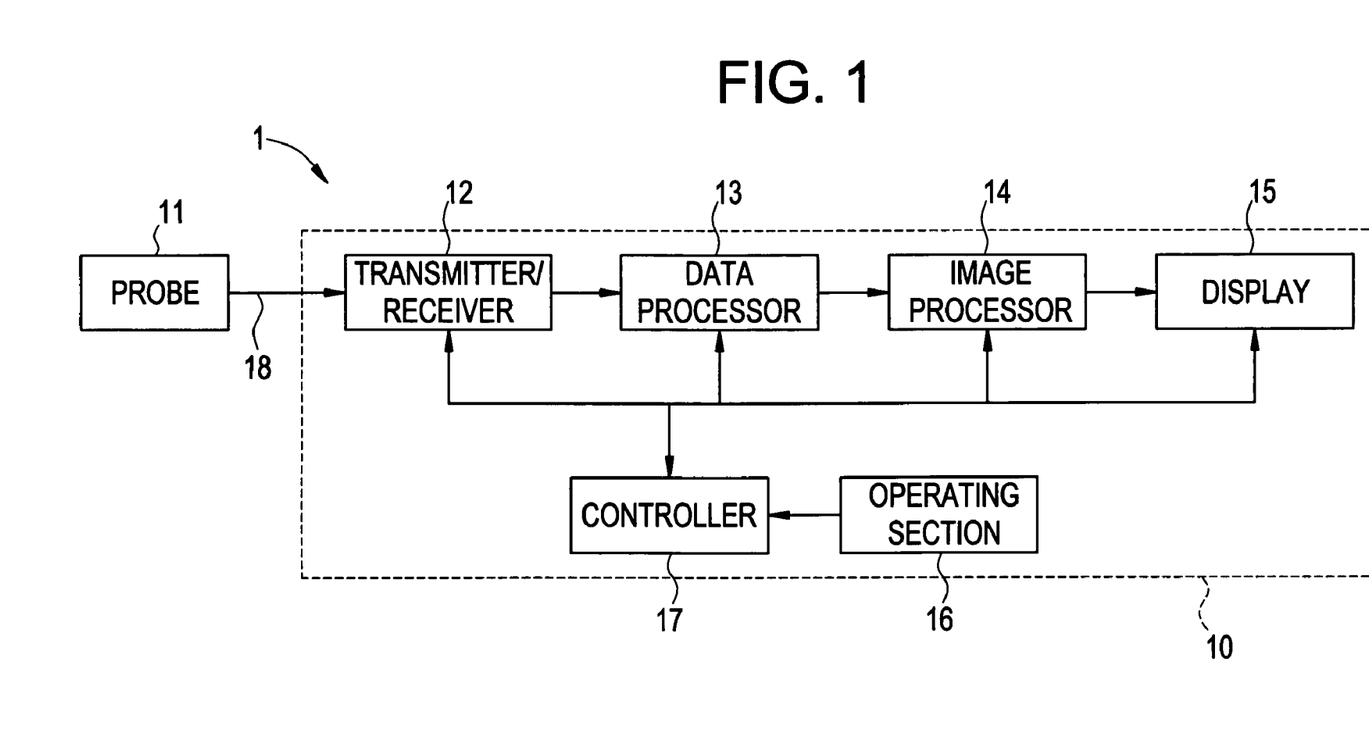
FIG. 1 is a block diagram showing the configuration of an ultrasonic diagnostic system according to an embodiment of the present invention.

FIG. 1 is a block diagram showing an entire configuration of an ultrasonic diagnostic system 1 according to an embodiment of the present invention. The ultrasonic diagnostic system 1 includes a probe 11, the probe 11 converting an electric signal to an ultrasonic wave, transmitting the ultrasonic wave to a subject, then receiving the ultrasonic wave reflected from the subject and converting the received ultrasonic wave to an electric signal, and a system body 10 which forms an image of the subject on the basis of a signal provided from the probe.

The system body 10 includes a transmitter/receiver 12 for transmission and reception of electric signals to and from the probe 11, a data processor 13 which for example generates image data on the basis of a signal provided from the transmitter/receiver 12, an image processor 14 which outputs a signal based on the image data produced by the data processor 13, a display 15 which displays an ultrasonic image on the basis of a signal provided from the image processor 14, an operating section 16 for an input operation by a user, and a controller 17 which controls the components 12 to 15 in accordance with a signal, etc. provided from the operating section 16.

The transmitter/receiver 12 is connected to the probe 11 through a cable 18. In accordance with a command provided from the controller 17 the transmitter/receiver 17 transmits a drive signal to the ultrasonic probe 11 through the cable 18. Further, the transmitter/receiver 12 receives an echo signal from the probe 11, then performs a processing such as amplification for the received echo signal and outputs the thus-processed signal to the data processor 13.

The data processor 13 is constituted for example by a computer and in accordance with a command issued from the controller 17 it processes the signal provided from the transmitter/receiver 12 and generates data for an ultrasonic image of a subject. For example, the data processor 13 performs a logarithmic amplification for the echo signal outputted from the transmitter/receiver 12, then detects an envelope and generates image data of B mode. Further, for example, the data processor 13 generates image data successively at a predetermined timing and stores the generated image data into memory (not shown), whereby it becomes possible to effect a three-dimensional dynamic image display (4D imaging) or the like.

The image processor 14 is constituted for example by a computer and in accordance with a command issued from the controller 17 it generates a signal for display of an ultrasonic image on the display 15 on the basis of image data outputted from the image processor 14 or image data stored in memory (not shown), then outputs the signal to the display 15.

The display 15 is constituted for example by a CRT display and has a screen for the display of an ultrasonic image. The operating section 16 is provided with, for example, a keyboard and a pointing device and in accordance with an input operation it outputs a signal to the controller 17.

The controller 17 is constituted for example by a computer and is connected to all of the probe 11, transmitter/receiver 12, data processor 13, image processor 14 and display 15. In accordance with an operation signal provided from the operating section 16 the controller 17 provides control signals to the components to control the operations of the components.

Figure 2A:
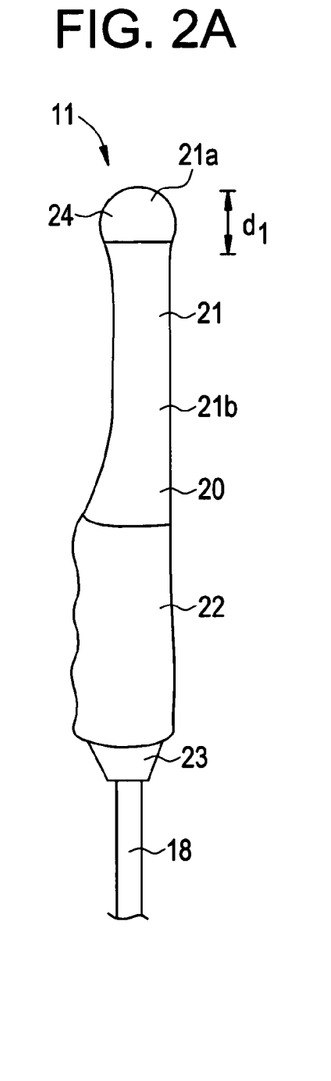
FIGS. 2a and 2b are diagrams showing a probe of the ultrasonic diagnostic system FIG. 1.
Figure 2B:
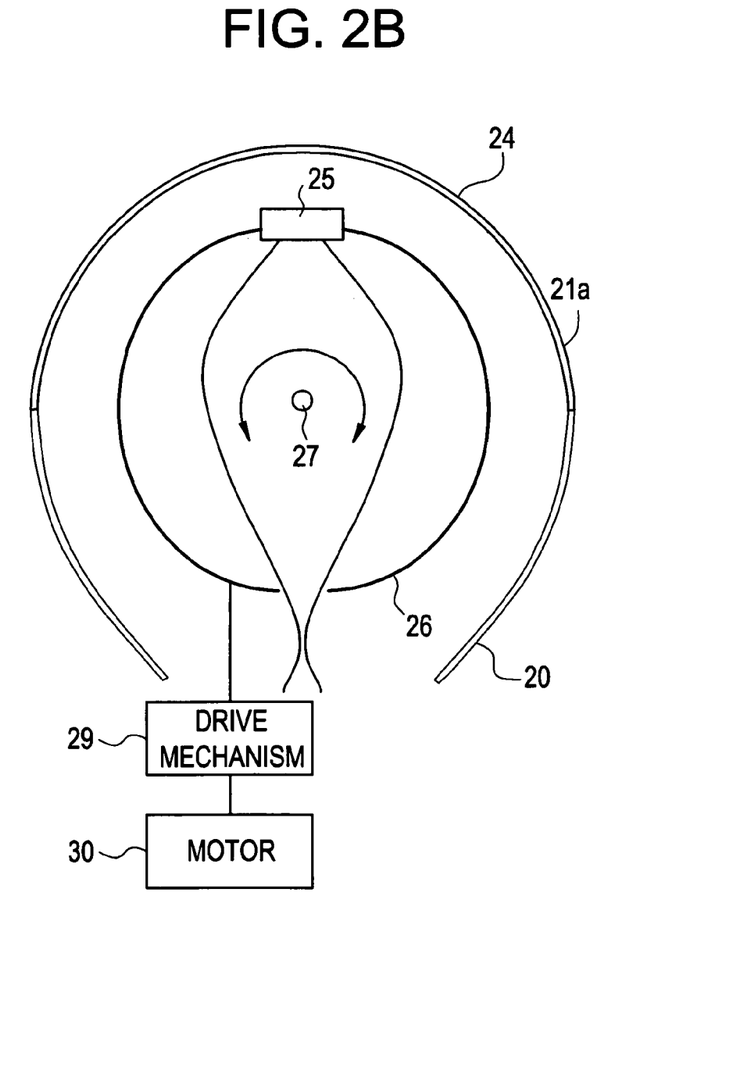

FIG. 2(a) is a plan view showing an appearance of the probe 11 and FIG. 2(b) is a sectional view showing a part of an internal configuration of the probe 11.

As shown in FIG. 2(a), the probe 11 is formed in an elongated shape as a whole and is constituted as a probe for the body cavity to be inserted from for example the anus into the body cavity. The probe 11 is provided with a case 20 which defines an outline. The case 20 includes an inserting portion 21 to be inserted into the body cavity, a grip portion 22 to be gripped by a user, and a bushing portion 23 from which the cable 18 extends.

The inserting portion 21 includes a spherical tip portion 21a and a cylindrical rod portion 21b. The diameter and length of the inserting portion 21 are set to appropriate sizes which permit insertion of the inserting portion into the body cavity. A part of the tip portion 21a and the rod portion 21b are integrally formed by molding with use of a rigid resin for example. An outer cover 24 is provided in the tip portion 21a. The probe 11 transmits and receives an ultrasonic wave through the outer cover 24.

The grip portion 22 is formed in a generally cylindrical shape having a diameter larger than that of the inserting portion 21. The diameter and length of the grip portion 22 are set to sizes which permit the grip portion to be easily gripped by one hand. Further, to facilitate the gripping, the grip portion 22 is formed with concaves and convexes in conformity with the positions of the fingers. The grip portion 22 is formed of a rigid resin for example.

The bushing portion 23 is formed of a material lower in rigidity than the grip portion 22 and higher in rigidity than the cable 18, e.g., a soft resin or rubber. The cable 18 is fitted through the bushing portion 23 to prevent the cable from being bent or pulled out.

As shown in FIG. 2(b), the probe 11 includes a transducer 25 for interconversion between an ultrasonic wave and an electric signal, a shell (holding member) 26 for holding the transducer 25, and a pivot shaft 27 for supporting the shell 26 pivotably with respect to the case 20.

By moving the shell 26 pivotally about the pivot shaft 27, the transducer 25 also moves pivotally and there is performed a mechanical scan by the probe 11. The range of the scan is set to a predetermined angle range in both clockwise and counterclockwise directions in FIG. 2(b), centered on the position where the transducer 25 faces the tip portion of the case 20. The transducer 25 is protected by the outer cover 24 and is not put in direct contact with the subject. The outer cover 24 is bonded closely without any gap to the rod portion 21b side of the tip portion 21.

The driving force of a motor 30 (a driving unit) is transmitted to the shell 26 by a drive mechanism 29, whereby the shell 26 is driven. A suitable mechanism may be utilized as the drive mechanism 29. For example, the rotation of the motor 30 may be transmitted to the shell 26 through a belt or a shaft. The drive of the motor 30 is controlled for example by a motor driver (not shown) disposed within the case 20 in accordance with a control signal provided from the controller 17. Rotational direction, speed and quantity of the motor 30 are set to appropriate values according to scan conditions of the probe 11.

For example, the cable 18 includes a coaxial cable 33 extending from the transducer 25. The coaxial cable 33 extends from the shell 26 and is fixed by the bushing portion 23. The length of the coaxial cable 33 from the transducer 25 to the bushing portion 23 is set so as to ensure a play between the transducer 25 and the bushing portion 23, that is, so as to permit rotation of the shell 26. The bushing portion 23 functions as a cable fixing portion. For example, however, a clip portion for clipping the coaxial cable 33 may be provided in the interior of the inserting portion 21 and may be used as a cable fixing portion. In the interior of the case 20 the coaxial cable 33 may be connected to another cable and the another cable may be extended out from the bushing portion 23.

Figure 3:
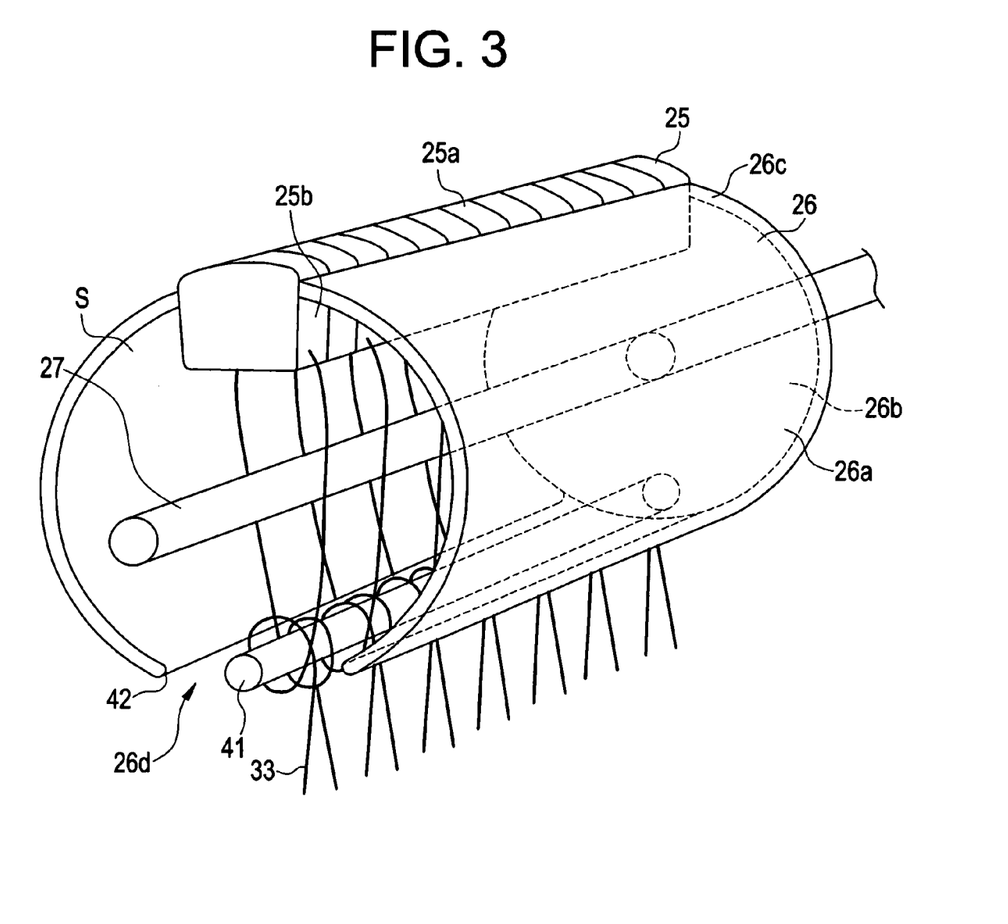
FIG. 3 is a diagram showing an internal configuration of a tip portion of the probe of FIG. 2.

FIG. 3 is a perspective view showing the interior of the tip portion 21a of the probe 11. In FIG. 3, a part of the shell 26 is shown in a broken-away condition.

The shell 26 is formed in a generally cylindrical shape as a whole and is provided with a side face 26a which defines a cylindrical hollow portion S and end faces 26b which close ends of the hollow portion S. In FIG. 3, the end face 26b located on this side in the same figure is omitted. The pivot shaft 27 is inserted so as to extend through the centers of the end faces 26b. In other words, the shell 26 is formed in a cylindrical shape around the pivot shaft 27. For example, the shell 26 is formed of a rigid resin.

A mounting portion 26c for the transducer 25 is provided in the side face 26a of the shell 26 at an upper position in FIG. 3. For example, an elongated hole extending axially of the pivot shaft 27 is formed in the mounting portion 26c. The transducer 25 is fitted in the elongated hole and is held by the shell 26 in a state in which a transmission/reception surface 25a thereof is exposed to the outside of the shell 26.

The plurality of transducers 25 are disposed along the elongated hole, i.e., axially of the pivot shaft 27. The number of the plural transducers 25 is, for example 192. The transducers 25 are each constituted, for example, by a transducer with acoustic lens and each include a piezoelectric element such as PZT (lead titanate zirconate) ceramic material.

A guide portion 26d for guiding the coaxial cable 33 is formed in the side face 26a of the shell 26 at a position (a lower position in FIG. 3) opposed to the mounting portion 26c with respect to the pivot shaft 27. In the guide portion 26d there are provided a guide bar 41 on which the coaxial cable 33 is wound and a slot 42 through which the coaxial cable 33 is inserted.

The guide bar 41 is formed in a cylindrical shape parallel to the axis of the pivot shaft 27 with use of a rigid resin for example. The guide bar 41 is disposed at a position opposed to the transducers 25 with respect to the pivot shaft 27. The guide bar 41 is positioned centrally of the slot 42 in the transverse direction (a direction orthogonal to the axis of the pivot shaft 27, i.e., the right and left direction in FIG. 3) of the slot. Further, in the radial direction of the shell 26 the guide bar 41 is positioned somewhat on the interior side of the shell with respect to the slot 42.

The guide bar 41 has a length which covers the plural transducers 25 in the axial direction of the pivot shaft 27. For example, the diameter of the guide bar 41 is set larger than the thickness of the side face 26a. The diameter of the guide bar 41 is set in consideration of various conditions, including the diameter of the coaxial cable 33 and the size and rotational range of the shell 26. For example, in the case where the diameter d1 (see FIG. 2) of the tip portion 21a is 24-26 mm and the diameter of the coaxial cable 33 is about 1 μm, the diameter of the guide bar 41 is about 1 mm.

The slot 42 is formed in the shape of an elongated hole extending axially of the pivot shaft 27. Like the guide bar 41, the slot 42 has a length which covers the plural transducers 25 in the axial direction of the pivot shaft 27. For example, the width of the slot 42 is set to a value larger than the total length of the diameter of the guide bar 41 plus the diameters of two coaxial cables 33. Plural coaxial cables 33 are wound round the guide bar 41 extend to the exterior of the shell 26 without being clipped by the slot 42.

Each coaxial cable 33 extend from a side face 25b of the associated transducer 25 toward the interior of the shell 26. The coaxial cable 33 is wound round the guide bar 41 and extends to the exterior of the shell 26 through the slot 42. The coaxial cable 33 is wound with a margin round the guide bar 41. In other words, the length of the coaxial cable 33 from the transducer 25 to the bushing portion 23 is set in such a manner that the coaxial cable 33 can be wound with a margin round the guide bar 41.

The plural coaxial cables 33 are arranged in such a manner that the coaxial cables 33 extending from the side face 25b on one side (this side in FIG. 3) and the coaxial cables 33 extending from the side face 25b on the opposite side (the inner side in the same figure) are alternate with each other in the arranged direction of the transducers 25. Adjacent coaxial cables 33 are wound in mutually opposite directions round the guide bar 41.

More specifically, the coaxial cables 33 extending from the side face 25b on one side pass one side with respect to the pivot shaft 27, then reach one side of the guide bar 41 and are wound round the guide bar in the order of the exterior side of the shell 26, the opposite side, the interior side of the shell 26 and one side (clockwise in FIG. 3). On the other hand, the coaxial cables 33 extending from the side face 25b on the opposite side pass the opposite side with respect to the pivot shaft 27, then reach the opposite side of the guide bar 41 and are wound round the guide bar 41 in the order of the exterior side of the shell 26, one side, the interior side of the shell 26 and the opposite side (counterclockwise in FIG. 3).

The following description is now provided about a mechanical operation of the probe 11 which is performed in response to a mechanical scan in the ultrasonic diagnostic system 1.

Reference will first be made to a comparative example. FIG. 4 shows an operation of a probe 11' in the absence of the guide bar 41. In the probe 11', each coaxial cable 33 is clipped by a slot 42'. The reason why each coaxial cable 33 is clipped by the slot 42' is that it is intended to prevent a load from being imposed on the connection between the coaxial cable 33 and the associated transducer 25.

Figure 4A:
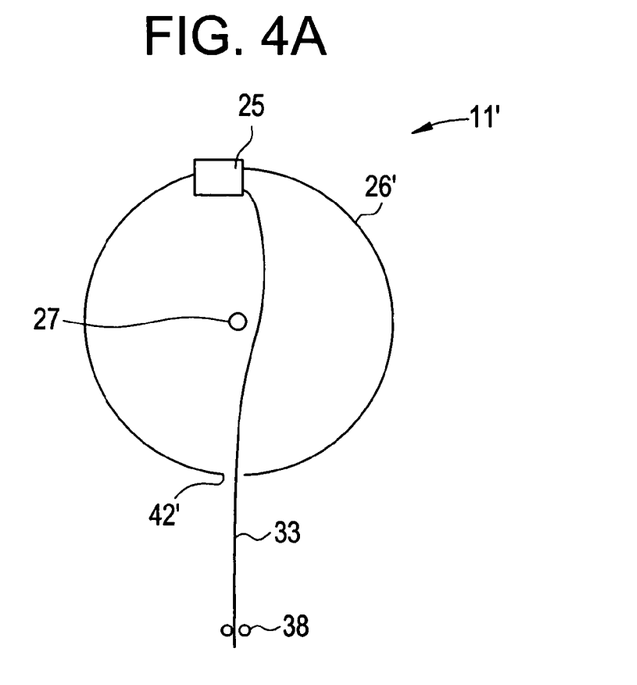
FIGS. 4a and 4b are diagrams showing the operation of a probe as a comparative example.
Figure 4B:
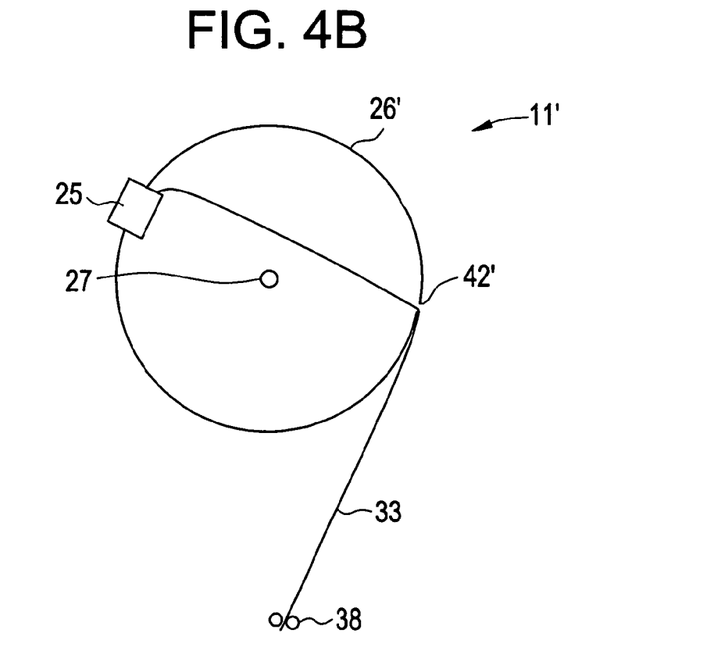

As shown in FIG. 4(a), when a shell 26' is in a neutral position, the transducer 25, slot 42' and clip portion 38 extend in a generally rectilinear shape and the coaxial cable 33 extend in a generally rectilinear shape from the transducer 25 to the clip portion 38. However, as shown in FIG. 4(b), when the shell 26' is driven for rotation, the coaxial cable 33 is bent by the slot 42'. Besides, the path from the transducer to the clip portion 38 becomes longer, which may result in a large tension being developed in the coaxial cable 33.

FIG. 5 shows an operation of the probe 11 in the presence of the guide bar 41, i.e., the probe 11 used in the diagnostic system 1.

Figure 5A:
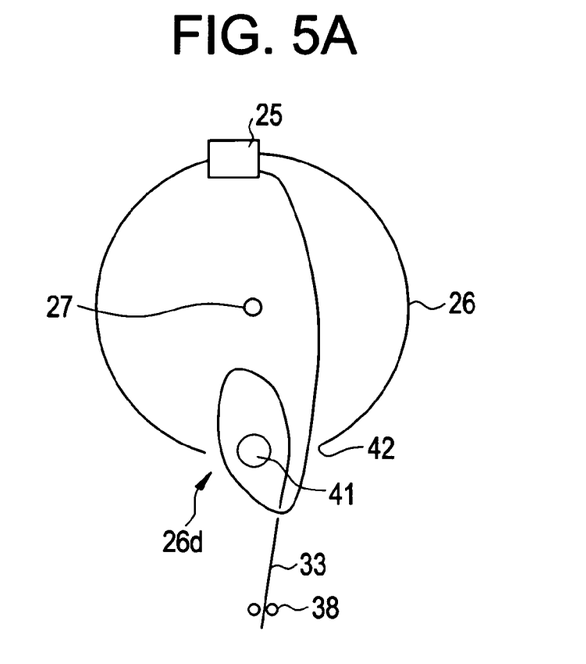
FIGS. 5a and 5b are diagrams showing the operation of the probe of FIG. 2.

As shown in FIG. 5(a), when the shell 26 is in its neutral position, the transducer 25, the guide portion 26d and the clip portion 38 are arranged in a generally rectilinear shape. Each coaxial cable 33 is in a wound state round the guide bar 41 with a relatively large margin. In other words, a ring formed around the guide bar 41 by the coaxial cable 33 is relatively large.

Figure 5B:
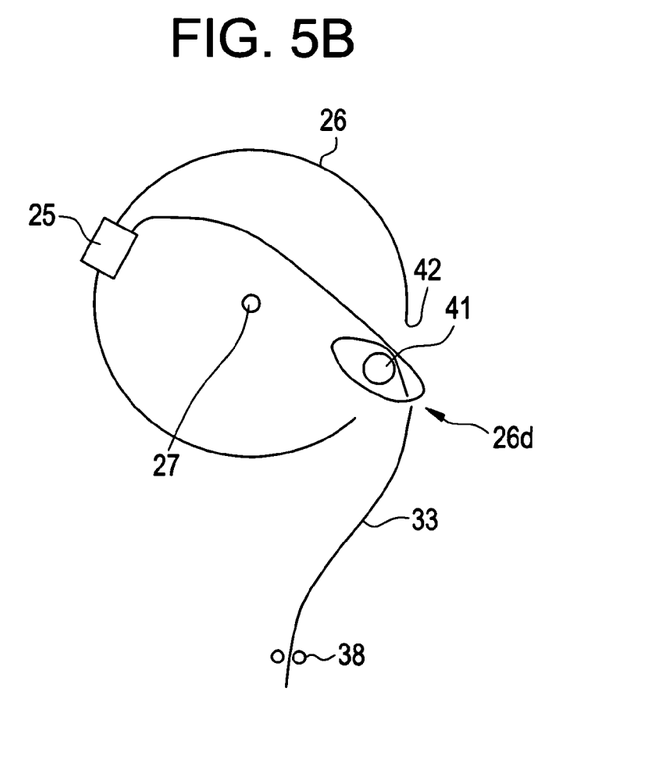
Figure 6:
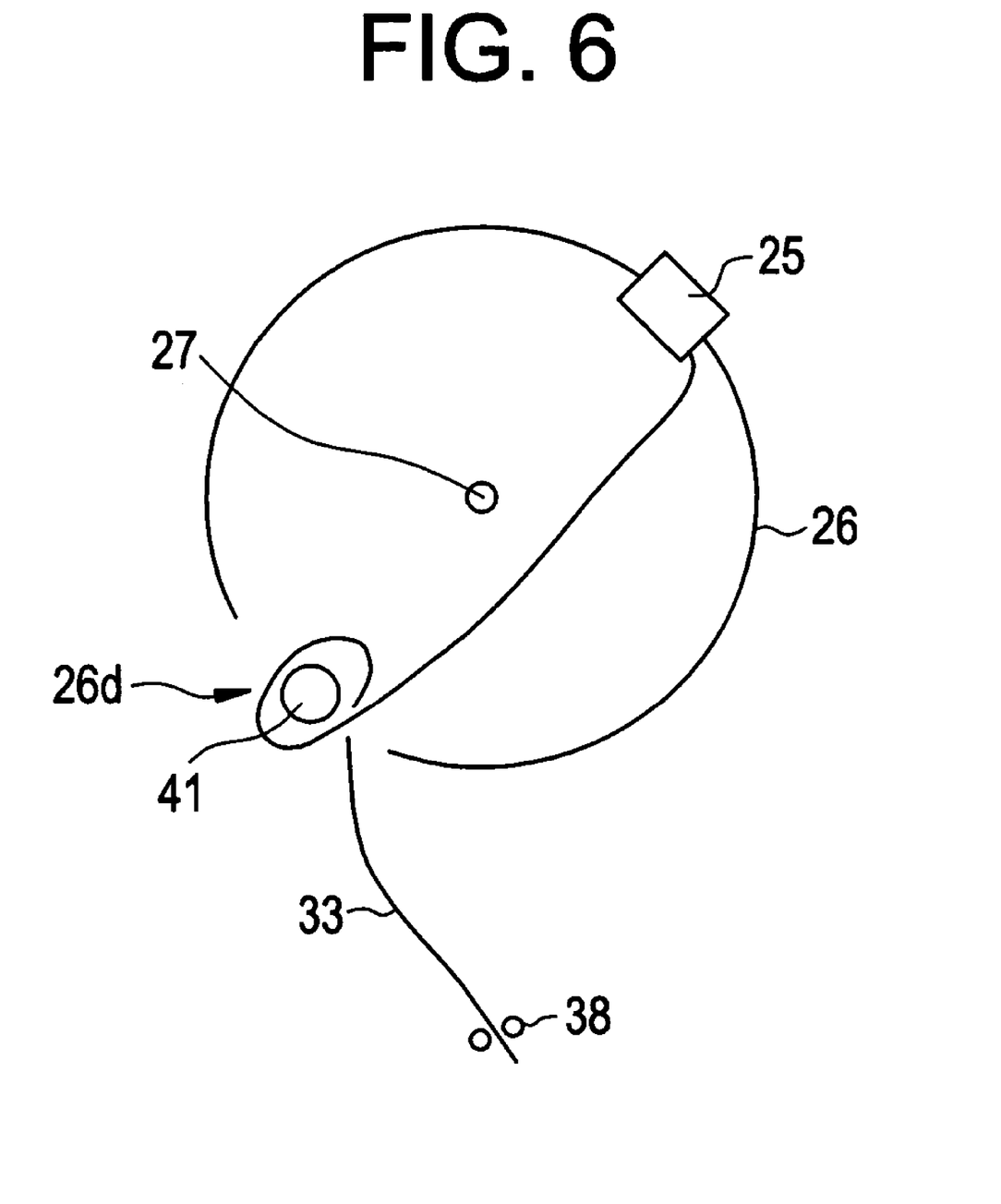
FIG. 6 is a diagram showing the operation of the probe of FIG. 2.

As shown in FIG. 5(b), even when the shell 26 is driven for rotation, the coaxial cable 33 is supported by the guide bar 41 while forming a ring around the guide bar and is therefore not bent. The ring of each coaxial cable 33 around the guide bar 41 becomes smaller to cope with an increase in length of the path from the associated transducer to the clip portion 38, so that the development of a tension in the coaxial cable 33 is also suppressed. Further, as shown in FIG. 6, also when the shell 26 is rotated in the direction opposite to the rotational direction shown in FIG. 5(b), the coaxial cable 33 is supported mainly by the guide bar 41, whereby bending of the coaxial cable and the development of a tension thereof are suppressed.

According to this embodiment, since the guide bar 41 is provided and the coaxial cables 33 are wound round the guide bar 41, the coaxial cables 33 are guided to the exterior of the shell 26 while forming rings around the guide bar, whereby bending of the coaxial cables is suppressed.

Since the coaxial cables 33 are wound with a margin around the guide bar 41, they can each change the size of the ring around the guide bar 41 with rotation of the shell 26 to cope with a change in length of the path from the associated transducer 25 to the bushing portion 23, whereby the development of a tension in the coaxial cable 33 is also suppressed.

The guide bar 41 has a circular sectional shape and the curvature of each coaxial cable 33 is suppressed even as a minimum to the same size as the curvature of the circumference of the guide bar 41. Moreover, since the diameter of the section of the guide bar 41 is set larger than the thickness of the side face 26a of the shell 26 in the vicinity of the slot 42, the cable curvature does not becomes smaller than the curvature when bent in abutment against an edge portion of the slot 42.

Since adjacent ones of the plural coaxial cables 33 are wound in mutually opposite directions, the load applied from each coaxial cable 33 to the associated transducer 25 and the guide bar 41 becomes symmetric right and left with respect to the neutral position, whereby the occurrence of an offset in the speed, etc. of the mechanical scan by the motor 30 is suppressed.

The probe 11 is used in an inserted state into the body cavity of a subject, and for such a relatively small probe, the design of the slot 42 in the shell 26 is required to be precise for preventing the occurrence of bending, etc. of each coaxial cable 33. In this embodiment, however, since the guide bar 41 is provided to suppress the occurrence of such bending as described above, the degree of design freedom of the slot 42 is improved.

The present invention is not limited to the above embodiment, but may be carried out in various other modes.

The probe is not limited to the type to be inserted into the body cavity, but may be one to be used in abutment against the body surface of a subject. The transducers are not limited to the plurally arranged transducers, but there may be used what is called a single array transducer.

The cable connected to each transducer is not limited to the coaxial cable. Any cable is employable insofar as it can effect the transfer of an electric signal to the transducer and the transfer of an electric signal from the transducer. For example, FPC may be used.

The holding member is not limited to a cylindrical one. Any other shape of a holding member is employable insofar as the transducer(s) and the guide bar are provided and the holding member used is pivotable with respect to the case member.

The guide bar 41 need not always be parallel to the pivot shaft of the holding member. Even if the guide bar 41 is somewhat inclined relative to the pivot shaft, it is possible to suppress bending each cable caused by the pivotal movement of the holding member. For example, the guide bar 41 may be inclined about 30° relative to the pivot shaft. However, bending of the cable can be suppressed to the greatest extent in the case where the guide bar 41 is mounted in parallel with the pivot shaft. When the probe includes plural transducers arranged axially of the pivot shaft, it is preferable for the guide bar to be disposed in parallel with the pivot shaft so that design conditions, etc. of the plural transducers and cables become coincident.

The sectional shape of the guide bar is not limited to the circular shape. For example, even if the guide bar is formed in a polygonal shape having a triangular section whose vertex angle is relatively acute, bending does not occur if the cables are wound with a margin around the guide bar because the cables form rings around the guide bar. In this case, the diameter of the guide bar may be relatively small. For example, the guide bar diameter may be smaller than the shell thickness in the vicinity of the slot.

On the other hand, in the case where the guide bar is formed to have a section of a circular or elliptic shape or a polygonal shape of a relatively obtuse vertex angle, it is not always necessary for the cables to be wound with a margin around the guide bar because the curvature of each cable is kept to the curvature of the guide bar even if the cable is wound tight around the guide bar.

Each cable may be wound so as to straddle both pivot shaft and guide bar or may be wound first round the pivot shaft and then round the guide bar. The number of turn of each cable is not limited to one. However, from the standpoint of easiness of work and ensuring a space for receiving the wound cables therein, it is preferable that the number of turn be one.

It suffices for the plural cables to be each wound round the guide bar. Between adjacent cables, their extending positions from the transducers or winding directions for the guide bar need not always be opposite. At least one of such extending positions and winding directions may be the same.

It is optional whether the slot of the holding member is to be utilized or not to be utilized as a clip for the cables. The position of the guide bar may be set to a suitable position relative to the slot insofar as bending of the cables in the slot is suppressed by the guide bar. Although in the above embodiment the guide bar is disposed somewhat on the inner side of the shell relative to the slot, it may be disposed at the same position as the slot or may be positioned on the outer side of the shell relative to the slot. That is, the position of the guide bar in the slot is not specially limited if only it is a position overlapping the slot in the circumferential direction of the cylinder and at that position the guide bar is exposed from the slot. For example, even if the cables are clipped by the slot of the shell, the occurrence of bending by the slot is suppressed if the cables are wound round the guide bar immediately outside the slot.

The invention claimed is:

1. An ultrasonic probe comprising:
    a transducer for interconversion between an ultrasonic wave and an electric signal; a holding member for holding the transducer;
    a case member for accommodating the holding member;
    a driving unit for moving the holding member pivotally about a predetermined pivot shaft with respect to the case member;
    a guide bar provided in the holding member so as to extend substantially in parallel with the pivot shaft; and
    a cable extending from the transducer to the guide bar, wound round the guide bar and then extending out from the holding member.

2. An ultrasonic probe according to claim 1, wherein:
    the case member has a cable fixing portion for fixing the cable extending out from the holding member; and
    the length of the cable from the transducer to the cable fixing portion is set so that the cable is wound with a margin round the guide bar.

3. An ultrasonic probe according to claim 1, wherein:
    the holding member is formed in the shape of a cylinder around the pivot shaft;
    the transducer is provided in a side face of the cylinder;
    a slot is formed in the side face of the cylinder at a position opposite to the transducer;
    the guide bar is provided in the slot at a position where it is exposed from the slot; and
    the cable passes through the inside of the cylinder from the transducer, extends to the guide bar and is wound round the guide bar, then extends to the outside of the cylinder from the slot.

4. An ultrasonic probe according to claim 3, wherein a sectional shape of the guide bar is a circular shape having a diameter larger than the thickness of the side face of the cylinder in the slot.

5. An ultrasonic probe according to claim 1, wherein:
the plurality of transducers are provided in the axial direction of the pivot shaft;
the plurality of cables are provided corresponding respectively to the plural transducers; and
the guide bar has such a length as covers the plural transducers in the axial direction of the pivot shaft.

6. An ultrasonic probe according to claim 5, wherein adjacent ones of the plural cables are wound in mutually opposite directions round the guide bar.

7. An ultrasonic probe according to claim 1, wherein:
the case member has an inserting portion capable of being inserted into the body cavity of a subject; and
the holding member is accommodated in a tip of the inserting portion.

8. An ultrasonic diagnostic system comprising:
a probe for radiating an ultrasonic wave to a subject and receiving the ultrasonic wave reflected from the subject; and
a system body for generating an image of the subject on the basis of a signal provided from the probe,
the probe comprising:
a transducer for interconversion between an ultrasonic wave and an electric signal;
a holding member for holding the transducer;
a case member for accommodating the holding member;
a driving unit for moving the holding member pivotally about a predetermined pivot shaft with respect to the case member;
a guide bar provided in the holding member so as to extend substantially in parallel with the pivot shaft; and
a cable extending from the transducer to the guide bar, wound round the guide bar and then extending out from the holding member.

\* \* \* \* \*